United States Patent

Sugiya et al.

Patent Number: 6,121,494
Date of Patent: Sep. 19, 2000

[54] METHOD OF PRODUCING OPTICALLY ACTIVE VINYL PHOSPHINE OXIDE

[75] Inventors: Masashi Sugiya, Tokyo; Hiroyuki Nohira, Urawa, both of Japan

[73] Assignee: Nippon Chemical Industrial Co., Ltd., Tokyo, Japan

[21] Appl. No.: 09/457,296

[22] Filed: Dec. 9, 1999

[30] Foreign Application Priority Data

Mar. 1, 1999 [JP] Japan ................... 11-053003

[51] Int. Cl.$^7$ ...................................................... C07F 9/53
[52] U.S. Cl. ................................................ 568/14; 568/17
[58] Field of Search ................... 568/13, 14, 17

[56] References Cited

U.S. PATENT DOCUMENTS

| | | | |
|---|---|---|---|
| 3,299,015 | 1/1967 | Miller | 526/78 |
| 3,495,257 | 2/1970 | Vullo | 568/14 |
| 4,365,094 | 12/1982 | Boileau et al. | 568/14 |

OTHER PUBLICATIONS

Tetrahedron Lett by Lam at al vol. 37 No. 27 pp. 4733–4736, 1996.
J Org Chem by Pietrusiewicz et al vol. 49 pp. 1522–1526, 1984.
Tetrahedron Lett by Pietrusiewicz et al vol. 30 No. 4 pp. 477479, 1989.
J Org Chem by Johnson et al vol. 52 pp. 2170–2174, 1987.
CA:105:227015 abs of SU 1253978, Aug. 1986.

*Primary Examiner*—Jean F Vollano
*Attorney, Agent, or Firm*—Armstrong, Westerman, Hattori, McLeland & Naughton

[57] ABSTRACT

Reacting a lead tetraacetate with an optically active phosphine oxide carboxylic acid represented by the following general formula (1):

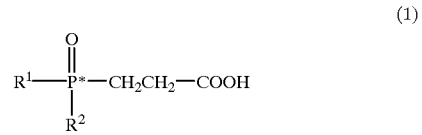

(1)

in order to obtain an optically active vinyl phosphine oxide represented by the following general formula (2):

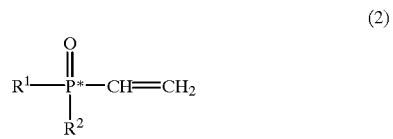

(2)

4 Claims, No Drawings

METHOD OF PRODUCING OPTICALLY ACTIVE VINYL PHOSPHINE OXIDE

BACKGROUND OF THE INVENTION

1. Field of the Invention

The present invention relates to a novel method of producing a vinyl phosphine oxide having high optical activity, which is useful as a material for producing optically active compounds.

2. Description of the Prior Art

Recently, the ratio of the optically active medicine of all the medicine in the market is increasing year after year. In the last five years, the optically active medicine amounted to 39% of the share. Moreover, the need for optically active substances is not limited to the field of medicine, but extends to fields such as agricultural chemicals, perfume, sweetener, seasoning, and even high-performance materials such as ferroelectric liquid crystal and packings for high performance liquid chromatography.

Being a functional group having high reactivity, the vinyl bonding is known to be especially useful as a building block in producing novel optically active compound having its asymmetric center on a phosphorus atom (K. M. Pietrusiewicz, M. Zablocka, and W. Wiesniewski, Phosphorus, Sulfur, and Silicon, 1990, 49/50, 263–266).

As a conventional method of producing an optically active vinyl phosphine oxide, a method is proposed, for example, as shown in the general formula mentioned below;

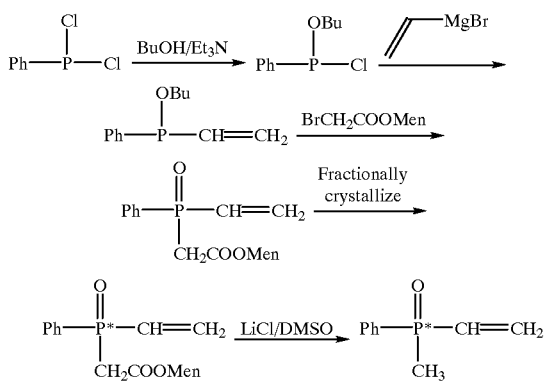

wherein phenyldichlorophosphane is reacted with butanol under the presence of triethylamine, and then Grignard reaction is performed using vinylmagnesium bromide. Next, the product is reacted with (−)-menthyl bromoacetate ester, recrystallized using benzene so as to fractionally crystallize the optically active substance, in order to obtain an optically active (−)-(mentoxy carbonylmethyl)phenyl vinyl phosphine oxide. Then, the result is subjected to reflux in dimethyl sulfoxide hydrate under the presence of lithium chloride at the temperature of 180° C. for two hours, so as to obtain the subject (−)-methyl phenyl vinyl phosphine oxide {(Ryszard Bodalski, Ewa rutkowska-Olma, Tetrahedron, 36, 2353–2355), (K. Michal Pietrusiewicz, Maria Zablocka, and Jaroslaw Monkiewicz, J. Org. Chem., 1984, 49, 1522–1526)}.

Also, as a method of producing optically active vinyl phosphine oxide having extremely high optical purity, Japanese Laid-Open Patent Publication No. S64-75495 discloses a method of contacting a racemic modification of a phosphine oxide class shown by the following general formula (3):

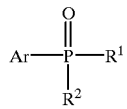

(3)

(in the formula, Ar represents an aryl group, $R^1$ and $R^2$ are a low-rank hydrocarbon group with 1–6 carbons which are dissimilar, with an example of vinyl group shown) to a 2,2-dihydroxy-1,1-binaphthyl in an organic solvent, and then separating and dividing the produced inclusion complex.

Also, the present inventors proposed in Japanese Patent Application No. H10-29803 a method of producing an optically active phosphine oxide carboxylic acid, wherein an optically active 1-phenyethylamine is reacted with a phosphine oxide carboxylic acid of a racemic modification shown by the following general formula (4):

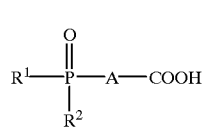

(4)

(in the formula, $R^1$ and $R^2$ represent a linear or branched alkyl group with 1–18 carbons, or a substituted or non-substituted phenyl group, and A represents an alkylene group, wherein $R^1$ and $R^2$ are of dissimilar groups), and a produced diastereomeric salt is separated using the difference in solubility against a solvent which is subsequently decomposed by acid, so as to obtain an optically active phosphine oxide carboxylic acid.

SUMMARY OF THE INVENTION

Upon careful study of the novel method of producing an optically active vinyl phosphine oxide, the present inventors discovered that when using the optically active phosphine oxide carboxylic acid disclosed in the Japanese Patent Application No. H10-29803 mentioned above which the present inventors suggested earlier as a reaction material, it is possible to obtain a vinyl phosphine oxide with high optical purity while maintaining asymmetric structure and without turning racemic, thereby completing the present invention.

The present invention provides the following:

A method of producing an optically active vinyl phosphine oxide characterized by reacting a lead tetraacetate with an optically active phosphine oxide carboxylic acid shown by the following general formula (1):

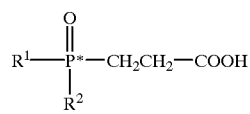

(1)

(in the formula, $R^1$ and $R^2$ represent a linear or branched alkyl group with 1–18 carbons, or a substituted or non-substituted phenyl group, wherein $R^1$ and $R^2$ are of dissimilar groups, and P* represents an asymmetric phosphorus atom), wherein said optically active vinyl phosphine oxide is shown by the following general formula (2):

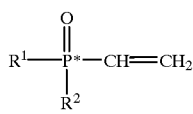

(2)

(in the formula, $R^1$, $R^2$ and $P^*$ represent what are defined above).

Moreover, it is preferable to perform the reaction under the presence of copper acetate and bases such as pyridine and trimethylamine.

PREFERRED EMBODIMENT OF THE INVENTION

The present invention will now be explained in detail.
Optically Active Phosphine Oxide Carboxylic Acid An optically active phosphine oxide carboxylic acid which is the reaction material of the present invention is represented by the above-mentioned general formula (1).

In the formula, $R^1$ and $R^2$ represent what are defined above, and the specific type of alkyl group may be any of the methyl group, ethyl group, n-propyl group, isopropyl group, n-butyl group, isobutyl group, n-pentyl group, isopentyl group, n-hexyl group, isohexyl group, n-heptyl, isoheptyl, n-octyl, isooctyl group, n-dodecyl group, isododecyl group and the like.

The examples of the specific compound of the optically active phosphine oxide carboxylic acid shown by the above-mentioned general formula (1) are as follows: (-)-(S)-[(2-carboxyethyl)(1,1,3,3-tetramethylbutyl)methyl]phosphine oxide, (+)-(R)-[(2-carboxyethyl)(1,1,3,3-tetramethylbutyl)methyl]phosphine oxide, (-)-(S)-[(2-carboxyethyl)(1,1,-dimethylethyl)methyl]phosphine oxide, (+)-(R)-[(2-carboxyethyl)(1,1,-dimethylethyl)methyl]phosphine oxide, (-)-(S)-[(2-carboxyethyl)(1,1,3,3-tetramethylbutyl)ethyl]phosphine oxide, (+)-(R)-[(2-carboxyethyl)(1,1,3,3-tetramethylbutyl)ethyl]phosphine oxide, (-)-(S)-[(2-carboxyethyl)(1,1,3,3-tetramethylbutyl)(1,1,-dimethylethyl)]phosphine oxide, (+)-(R)-[(2-carboxyethyl)(1,1,3,3-tetramethylbutyl)(1,1,-dimethylethyl)]phosphine oxide, (-)-(S)-[(2-carboxyethyl)(O-methoxyphenyl)phenyl]phosphine oxide, (+)-(R)-[(2-carboxyethyl)(O-methoxyphenyl)phenyl]phosphine oxide, (-)-(S)-[(2-carboxyethyl)(O-ethylphenyl)phenyl]phosphine oxide, or (+)-(R)-[(2-carboxyethyl)(O-ethylphenyl)phenyl]phosphine oxide.

Although the method of producing said optically active phosphine oxide carboxylic acid will not be limited, a method may preferably be used for example, as disclosed in Japanese Patent Application No. H10-29803 which the present inventors suggested earlier, wherein a racemic mixture shown by the following general formula (5):

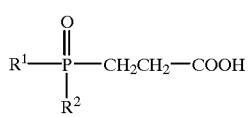

(5)

(in the formula, $R^1$ and $R^2$ represent what are defined above) is reacted with an amine such as an optically active 1-phenylethylamine to obtain diastereomeric salt, and the optically active substance is separated using the difference in solubility against a solvent.

Specifically, optically active 1-phenylethylamine which is a reagent for optical resolution may be added to racemic mixture of phosphine oxide carboxylic acid shown by the general formula (4) mentioned above, in a ratio of 0.7–1.0 mol per phosphine oxide carboxylic acid.

A reaction solvent to be used in the present invention may be acetone, methylethylketone, MIBK and the like of the ketone class, and especially, acetone and methylethylketone is preferred. The amount of said solvent to be used differs according to solubility, but generally, the appropriate amount should be five to ten times the amount (weight ratio) of the solute. The reaction is a neutralization reaction, so no special reaction condition is required. The method of mixing is also not specified, and it may either be mixed directly into the solvent, or each solution may be mixed together. A homogeneous solution is obtained at a reacting temperature of either the room temperature or a heated temperature below the boiling point of the solvent, and the solution is then deposited statically for the deposition of a refractory diastereomeric salt. The deposition temperature may either be room temperature or a temperature cooled by a cooler or a refrigerator. Normally at this state, inoculation of the seed crystal of the salt to be deposited is performed.

The deposited salt is separated from the solvent by filtration or centrifugal separation, and recrystallization and purification may be performed thereto according to need. The obtained salt is processed by strong acid such as hydrochloric acid or sulfuric acid so as to decompose the salt, and by performing extraction using a solvent which does not mix with water and capable of solving phosphine oxide carboxylic acid, an optically active phosphine oxide carboxylic acid may be obtained. Further, recrystallization and purification may be performed thereto according to need.

Lead Tetraacetate

As the other reaction material to be used in the method of producing the vinyl phosphine oxide according to the present invention, lead tetraacetate is not specified as long as it is industrially obtainable, so it may be hydrate or anhydride.

The method of producing the optically active vinyl phosphine oxide shown by the above-mentioned general formula (2) of the present invention involves performing an oxidation reaction to the optically active phosphine oxide carboxylic acid shown by the above-mentioned general formula (1) with lead tetraacetate in a solvent, characterized by obtaining a required (+) body or (-) body of the optically active vinyl phosphine oxide shown by the above-mentioned general formula (2), by reacting with lead tetraacetate a selected (+) body or (-) body of the optically active phosphine oxide carboxylic acid shown by the above-mentioned general formula (1).

The examples of the specific compound obtained from the method of producing the vinyl phosphine oxide according to the present invention are as follows: (-)-[(1,1,3,3-tetramethylbutyl)methylvinyl]phosphine oxide, (+)-[(1,1,3,3-tetramethylbutyl)methylvinyl]phosphine oxide, (-)-[(1,1,-dimethylethyl)methylvinyl]phosphine oxide, (+)-[(1,1,-dimethylethyl)methylvinyl]phosphine oxide, (-)-[(1,1,3,3,-tetramethylbutyl)ethylvinyl]phosphine oxide, (+)-[(1,1,3,3,-tetramethylbutyl)ethylvinyl]phosphine oxide, (-)-[(O-methoxyphenyl)phenylvinyl]phosphine oxide, (+)-[(O-methoxyphenyl)phenylvinyl]phosphine oxide, (-)-[(O-ethylphenyl)phenylvinyl]phosphine oxide, and (+)-[(O-ethylphenyl)phenylvinyl]phosphine oxide.

The amount of use of the lead tetraacetate should range between 0.1–2.0 times mol, preferably between 0.5–1.5 times mol against phosphine oxide carboxylic acid. Also, copper acetate should be used in a range of 0.01–1.0 times mol, preferably in a range of 0.1–0.5 times mol against lead tetraacetate. A copper acetate helps produce unsaturated ethylene by drawing out hydrogen cation from radical ion which is produced from oxidizing and decarboxylating the phosphine oxide carboxylic acid with lead tetraacetate. The copper acetate may either be anhydride or hydrate.

Also, in a method of producing the vinyl phosphine oxide according to the present invention, bases such as pyridine and triethylamine may be used as a catalyst according to need. In such case, the amount of catalyst to be used should be very small, and for example, it may range between 0.001–0.5 times mol, preferably between 0.05–0.2 times mol against lead tetraacetate.

As a reaction solvent, aromatic hydrocarbon such as benzene, toluene and xylene, aromatic hydrocarbon halide such as chlorobenzene, o-dichlorobenzene, m-dichlorobenzene, p-dichlorobenzene, 1,2,4-trichlorobenzene, o-chlorotoluene, p-chlorotoluene, bromobenzene, o-dibromobenzene, m-dibromobenzene, and p-dibromobenzene, aliphatic hydrocarbon such as hexane, heptane, and octane, and aliphatic hydrocarbon halide such as 1,2-dichloroethane, 1,1,1-trichloroethane, and trichloroethylene, are preferred.

Because the lead tetraacetate as the material turns brown by light, it is preferable to use a container or device which block light. Also, it is oxidized by air, so it is preferred to ventilate a fixed amount of inert gas such as nitrogen while performing the reaction. The reaction temperature varies according to the boiling point of the solvent to be used, but it should be set below the boiling point of the solvent, generally between 20–150° C., preferably between 50–100° C., and the reaction time is generally set between 0.5–24 hours, preferably between 1–5 hours.

The optically active vinyl phosphine oxide shown by the above-mentioned general formula (2) thus obtained has a high optical purity, and is useful as a reaction material for an optically active compound.

The present invention will now be explained in detail, though the present invention is not limited to the embodiments below.

EXAMPLE 1

Synthesis of [(2-carboxyethyl)(1,1,3,3-tetramethylbutyl) methyl]phosphine oxide Racemic Mixture A four-mouth flask having a capacity of 300 ml and equipped with an agitator, a thermometer, a dropping funnel and a condenser is sufficiently nitrogen-substituted, and 16.0 g (0.1 mol) of (1,1,3,3-tetramethylbutyl)methylphosphine and 15.6 g (0.15 mol) of concentrated hydrochloric acid are placed thereto. It is cooled and maintained at a temperature of 20–25° C., and 7.2 g (0.1 mol) of acrylic acid is dropped thereto. Thereafter, it is aged for two hours under a temperature of 40° C., concentrated by an evaporator, so as to remove excess hydrochloric acid therefrom. Further, 100 ml of high purity water is added thereto, which is then heated to 80° C., and 10.7 g (0.11 mol) of 35% hydrogen peroxide water is gradually dropped thereto while maintaining the temperature. It is further aged for three hours at the same temperature. The viscous solid obtained through concentration is recrystallized and purified by acetone to obtain 15.8 g of white-colored crystal having a melting point of 100–103° C. (yield of 63.8%). According to analysis results, this is a racemic mixture of [(2-carboxyethyl)(1,1,3,3-tetramethylbutyl)methyl]phosphine oxide.

$^1$H-NMR(ppm, CDCl$_3$): 1.06(s, 9H, CH$_3$), 1.35(d, 6H $J_{PCCH}$=17.6 Hz, CH$_3$), 1.50(d, 2H, CH$_2$, $J_{PCCH}$=8.6 Hz), 1.59(d, 3H, P—CH$_3$, $J_{PCH}$=11.7 Hz), 1.92–2.27(m, 2H, P—CH$_2$—), 2.57–2.80(m, 2H, —CH$_2$—COO), 11.81(s, 1H, COOH).

FAB-MASS(Pos.): m/z=249 [M+H$^+$]

FT-IR(KBr, cm$^{-1}$): 2953, 2918, 1735, 1422, 1233, 1171, 1112, 964, 903

UV-VIS(MeOH): $\epsilon_{max}$=140.1, $\lambda_{max}$=218.1 nm

Optical Resolution Part 1

In a flask having a capacity of 50 ml, 3.03 g (12.2 mmol) of the obtained [(2-carboxyethyl)(1,1,3,3-tetramethylbutyl) methyl]phosphine oxide from the above-mentioned example 1 and 4.5 ml of acetone is placed, and 1.48 g (12.2 mmol) of (+)-(R)-1-phenylethylamine is added thereto. It dissolved completely while generating little heat. The solution is statically deposited for twenty-four hours at 0° C., thereby depositing crystal. The crystal is then filtered and vacuum dried, so as to obtain 0.83 g of white-colored crystal. The crystal has a boiling point of 135–138° C., and the angle of rotation is $[\alpha]^{25}_D$=+3.42 (c 1.072 CH$_3$OH). This is freed by hydrochloric acid, and extracted by dichloromethane, so as to obtain 0.11 g of white-colored crystal. The crystal has a boiling point of 145–146° C., the angle of rotation of $[\alpha]^{25}_D$=−8.17 (c 1.04, methanol), and the substance is (−)-(S)-[(2-carboxyethyl)(1,1,3,3-tetramethylbutyl)methyl] phosphine oxide.

$^1$H-NMR(ppm, CDCl$_3$): 1.06(s, 9H, CH$_3$), 1.33(d, 6H $J_{PCCH}$=17.0 Hz, CH$_3$), 1.50(d, 2H, CH$_2$, $J_{PCCH}$=8.4 Hz), 1.49(d, 3H, P—CH$_3$, $J_{PCH}$=11.7 Hz), 1.78–2.16(m, 2H, P—CH$_2$—), 2.46–2.71(m, 2H, —CH$_2$—COO), 10.34(s, 1H, COOH).

FAB-MASS(Pos.): m/z=249 [M+H$^+$]

Optical Resolution Part 2

In a flask having a capacity of 50 ml, 3.05 g (12.3 mmol) of the obtained racemic mixture of [(2-carboxyethyl)(1,1,3, 3-tetramethylbutyl)methyl]phosphine oxide from the above-mentioned example 1 and 4.5 ml of acetone is placed, and 1.48 g (12.2 mmol) of (−)-(S)-1-phenylethylamine is added thereto. The solution is statically deposited for twenty-four hours at 0° C., thereby depositing crystal. The crystal is then filtered and vacuum dried, so as to obtain 0.32 g of white-colored crystal. The crystal has a boiling point of 126–131° C. This is freed by hydrochloric acid, and extracted by dichloromethane, so as to obtain 0.18 g of white-colored crystal. The crystal has a boiling point of 144–146° C., angle of rotation of $[\alpha]^{25}_D$=+6.30 (c=0.238, methanol), and the substance is (+)-(R)-[(2-carboxyethyl)(1,1,3,3-tetramethylbutyl)methyl]phosphine oxide.

$^1$H-NMR(ppm, CDCl$_3$): 1.06(s, 9H, CH$_3$), 1.33(d, 6H, $J_{PCCH}$=17.0 Hz, CH$_3$), 1.50(d, 2H, CH$_2$, $J_{PCCH}$=8.4 Hz), 1.49(d, 3H, P—CH$_3$, $J_{PCH}$=11.7 Hz), 1.83–2.22(m, 2H, P—CH$_2$—), 2.53–2.76(m, 2H, —CH$_2$—COO), 10.72(s, 1H, COOH).

FAB-MASS(Pos.): m/z=249 [M+H$^+$]

Embodiment 1

Synthesis of (+)-[(1,1,3,3-tetramethylbutyl)methylvinyl] phosphine oxide

In a four-mouth flask having a capacity of 300 ml and equipped with an agitator, a thermometer and a condenser, 5.03 g (20.3 mmol) of (−)-(S)-[(2-carboxyethyl)(1,1,3,3-tetramethylbutyl)methyl]phosphine oxide obtained in the above-mentioned optical resolution 1, 0.65 g (3.6 mmol) of copper acetate anhydride, 0.13 g (1.5 mmol) of pyridine, and 30 ml of chlorobenzene are placed, which are mixed for thirty minutes under room temperature so as to dissolve. Then, 8.9 g (20.1 mmol) of lead tetraacetate is added thereto under nitrogen current, and mixed so as to dissolve for one hour in a cool dark place. Then, it is heated to 80° C. under nitrogen current and reacted for seven hours and thirty minutes. After cooling, the solvent is concentrated by an evaporator, and chloroform and water are added thereto. Then, the chloroform layer is separated, and dehydration is carried out using sodium sulfate anhydride, which is then concentrated by an evaporator, thereby obtaining 4.64 g of green-colored liquid. This raw product is vacuum distilled to separate fraction of 80–85° C./3–4 mmHg, and 1.20 g of water-clear liquid is obtained. From analysis by gas chromatography, the purity of the liquid is 85.5% and distillation yield is 25.0%.

The optical purity of the liquid is measured using an optically active column CHIRALCEL OD-RH (product of Daisel Chemical Industry), an eluate of acetonitrile: water=

4:1, 0.5 ml/min, an UV detector (215 nm), and a temperature of 30° C., and the optical purity turned out to be 97.0% e.e. Also, the angle of rotation is $[\alpha]^{24}_D=+26.37$ (c=1.86, CHCl$_3$).

Embodiment 2

Synthesis of (−)-[(1,1,3,3-tetramethylbutyl)methylvinyl] phosphine oxide

By using (+)-(R)-[(2-carboxyethyl)(1,1,3,3-tetramethylbutyl)methyl]phosphine oxide obtained in optical resolution part 2, the reaction is carried out as in embodiment 1. In a four-mouth flask with a capacity of 300 ml and equipped with an agitator, a thermometer and a condenser, 7.30 g (29.4 mmol) of (+)-(R)-[(2-carboxyethyl) (1,1,3,3-tetramethylbutyl)methyl]phosphine oxide, 0.74 g (4.0 mmol) of copper acetate anhydride, 0.15 g (1.9 mmol) of pyridine, and 30 ml of chlorobenzene are placed, which are mixed for thirty minutes under room temperature so as to dissolve. Then, 13.25 g (29.9 mmol) of lead tetraacetate is added thereto under nitrogen current, and mixed so as to dissolve for one hour in a cool dark place. Further, it is heated to 80° C. under nitrogen current and reacted for three hours. After cooling, chloroform and water are added thereto. Then, the chloroform layer is separated, and dehydration is carried out using sodium sulfate anhydride, which is then concentrated by an evaporator, thereby obtaining 7.73 g of green-colored liquid. This raw product is vacuum distilled to separate fraction of 68–71° C./3 mmHg, and 2.12 g of water-clear liquid is obtained. From analysis by gas chromatography, the purity of the liquid is 91.5% and distillation yield is 32.6%.

By measuring the optical purity using optically active column CHIRALCEL OD-RH (product of Daisel Chemical Industry), an eluate of acetonitrile:water=4:1, 0.5 ml/min, an UV detector (215 nm), and a temperature of 30° C., the optical purity is 99.0% e.e. Also, the angle of rotation is $[\alpha]^{23}_D=-30.07$ (c 0.798, CHCl$_3$).

Comparative Embodiment

Synthesis of [(1,1,3,3-tetramethylbutyl)methylvinyl] phosphine oxide Racemic Mixture In a four-mouth flask with a capacity of 300 ml and equipped with an agitator, a thermometer and a condenser, 24.8 g (100.0 mmol) of [(2-carboxyethyl)(1,1,3,3-tetramethylbutyl)methyl]phosphine oxide which is a racemic mixture obtained in above-mentioned example 1, 455 mg (2.5 mmol) of copper acetate anhydride, 54.5 mg (6.6 mmol) of pyridine, and 30 ml of chlorobenzene are placed, which are mixed for thirty minutes so as to dissolve. Then, 21.5 g (46.5mmol) of lead tetraacetate is added thereto under nitrogen current, and mixed so as to dissolve for one hour in a cool dark place. Further, it is heated to 85° C. under nitrogen current and reacted for one hour and thirty minutes. After cooling, 200 ml of toluene is added thereto for dilution. Then it is washed with fixed amount of high purity water, and is further washed twice with saturated sodium bicarbonate solution. The organic solvent layer is separated, and dehydration is carried out using sodium sulfate anhydride, which is then concentrated with an evaporator in order to obtain 12.2 g of yellow green-colored liquid.

This raw product is vacuum distillated to separate fraction of 109–112° C./4 mmHg, and 6.4 g of water-clear liquid is obtained. From analysis by gas chromatography, the purity of the liquid is 93.4% and distillation yield is 31.6%.

The obtained yellow green-colored liquid is identified by $^1$H-NMR, $^{31}$P-NMR, FT-IR, GC-MS and UV analysis, and is confirmed to be a racemic mixture of (1,1,3,3-tetramethylbutyl)vinyl phosphine oxide.

Identification Data $^1$H-NMR (δ, CDCl$_3$): 1.052 (s, 9H), 1.305 (d, J=16.31 Hz, J=2.37 HZ, 6H), 1.451 (d, J =11.17 Hz, 3H), 1.564 (d, J=4.78 Hz, 2H), 6.147–6.339 (m, 3H).

$^{31}$P-NMR (δ, CDCl$_3$, Internal Standard; H$_3$PO$_4$):46.95(s)

FT-IR (liquid film, cm$^{-1}$):2953.5 (C—H stretch), 1474.3, 1389.5, 1366.3 (C—H inplane deformation), 1180.2 (P=O stretch), 989.3, 882.3 (C—H out-of-plane deformation).

GC-MASS(Pos.): m/z=202[M$^+$]

UV-VIS(MeOH): $\epsilon_{max}$=2300.6, $\lambda_{max}$=199.2 nm

According to the method of the present invention, an optically active vinyl phosphine oxide with high optical purity could be obtained easily through an industrially advantageous means. Further, the optically active vinyl phosphine oxide obtained in the present invention is advantageous as a reacting material for compounds requiring high optical purity.

We claim:

1. A method of producing an optically active vinyl phosphine oxide characterized by reacting a lead tetraacetate with an optically active phosphine oxide carboxylic acid shown by the following general formula (1):

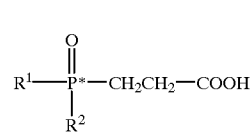

(1)

(in the formula, R$^1$ and R$^2$ represent a linear or branched alkyl group with 1–18 carbons, or a substituted or non-substituted phenyl group, wherein R$^1$ and R$^2$ are of dissimilar groups, and P* represents an asymmetric phosphorus atom), wherein said optically active vinyl phosphine oxide is shown by the following general formula (2):

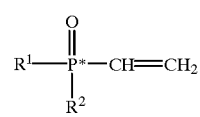

(2)

(in the formula, R$^1$, R$^2$ and P* represent what are defined above).

2. A method of producing an optically active vinyl phosphine oxide according to claim 1, wherein said reaction is carried out under the presence of a copper acetate.

3. A method of producing an optically active vinyl phosphine oxide according to claim 1 or 2, wherein said reaction is carried out under the presence of a bases.

4. A method of producing an optically active vinyl phosphine oxide according to claim 1 or 2, wherein reaction is carried out under the presence of a bases selected from pyridine and triethylamine.

* * * * *